United States Patent
Osaka (10) Patent No.: US 7,929,120 B2
(45) Date of Patent: Apr. 19, 2011

(54) APPARATUS FOR CONTROLLING OPTICAL FRINGE GENERATION MEMBER BASED ON DETECTED OPTICAL FRINGE AND METHOD THEREFOR

(75) Inventor: Tsutomu Osaka, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 459 days.

(21) Appl. No.: 12/030,106

(22) Filed: Feb. 12, 2008

(65) Prior Publication Data

US 2008/0291423 A1 Nov. 27, 2008

(30) Foreign Application Priority Data

Feb. 14, 2007 (JP) ................................ 2007-033496

(51) Int. Cl.
G01L 1/24 (2006.01)
G01B 11/02 (2006.01)
(52) U.S. Cl. .................... 356/35.5; 356/492; 356/496
(58) Field of Classification Search .............. 356/32, 356/33, 35.5, 492, 496
See application file for complete search history.

(56) References Cited

U.S. PATENT DOCUMENTS

| 4,789,236 A | * | 12/1988 | Hodor et al. | ................ | 356/33 |
| 5,410,917 A | * | 5/1995 | Giversen et al. | ................ | 356/33 |
| 5,723,794 A | * | 3/1998 | Discenzo | ................ | 73/800 |

FOREIGN PATENT DOCUMENTS

JP 04-352203 12/1992

OTHER PUBLICATIONS

Dubey et al, Optimal object grasp using tactile sensors and fuzzy logic, Robotica, vol. 17, 1999, pp. 685-693.*
Dubey et al, Extraction of load information from photoelastic images using neural networks, ASME 2006 proceedings of IDETO/CIE, Sep. 2006, pp. 1-7.*
Saad et al, Simplified theory of Tactile Sensing, Chapter 25-Tactile Sensing, , 1999, pp. 1-17.*

* cited by examiner

Primary Examiner — Patrick J Connolly
(74) Attorney, Agent, or Firm — Canon USA Inc IP Division (57) ABSTRACT

An optical fringe generation member control apparatus is provided. The control apparatus includes a detection unit that is configured to detect an optical fringe. Further, the control apparatus includes a control unit that is configured to control operation of a member on which the optical fringe is generated. The control unit controls the operation based on a detection result by the detection unit.

10 Claims, 12 Drawing Sheets

REACTION FORCE F

FIG. 11B

REACTION FORCE F

FIG. 11D

REACTION FORCE F

APPARATUS FOR CONTROLLING OPTICAL FRINGE GENERATION MEMBER BASED ON DETECTED OPTICAL FRINGE AND METHOD THEREFOR

CROSS-REFERENCE TO RELATED APPLICATIONS

This application claims priority from Japanese Patent Application No. 2007-033496 filed on Feb. 14, 2007, which is hereby incorporated by reference herein in its entirety.

BACKGROUND OF THE INVENTION

1. Field of the Invention

The present invention relates to an apparatus and method for controlling operation of a member that generates an optical fringe.

2. Description of the Related Art

To control operation of a robotic arm, it is necessary to detect a load applied to the robotic arm. Conventionally, in order to detect the load, a stress detection sensor is provided in the robotic arm. Based on an output from the stress detection sensor, the robotic arm is controlled. The stress detection sensor includes, for example, a stress sensor using a piezo element and a strain gauge. Japanese Patent Application Laid-Open No. 04-352203 discusses an apparatus that acquires a visible image of a robotic arm from a video camera image, and controls the robotic arm based on the acquired visible image.

However, according to the conventional technique, the more accuracy of the control apparatus that is required, the larger structure of the stress sensors becomes. Further, it is necessary to install the stress sensors in a contactor of the robotic arms. Accordingly, the structure of the apparatus becomes complicated.

While Japanese Patent Laid-Open No. 04-352203 discusses the apparatus that controls the robotic arm based on the video camera image, it is difficult to apply the apparatus to stress detection that requires accuracy, for example, in calculating stress at each part of the robotic arm or the like.

SUMMARY OF THE INVENTION

The present invention is directed to an optical fringe generation member control apparatus that controls operation of a subject member using a simple structure. The present invention is also directed to a method of controlling the optical fringe generation member control apparatus and a computer program for performing said method.

According to an aspect of the present invention, an optical fringe generation member control apparatus includes a member on which an optical fringe is generated, a detection unit configured to detect optical fringe, and a control unit configured to control operation of the member on which the optical fringe is generated, based on a detection result by the detection unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DETAILED DESCRIPTION OF THE EXEMPLARY EMBODIMENTS

Various exemplary embodiments, features, and aspects of the invention will be described in detail below with reference to the drawings.

First Exemplary Embodiment

Figure 1:
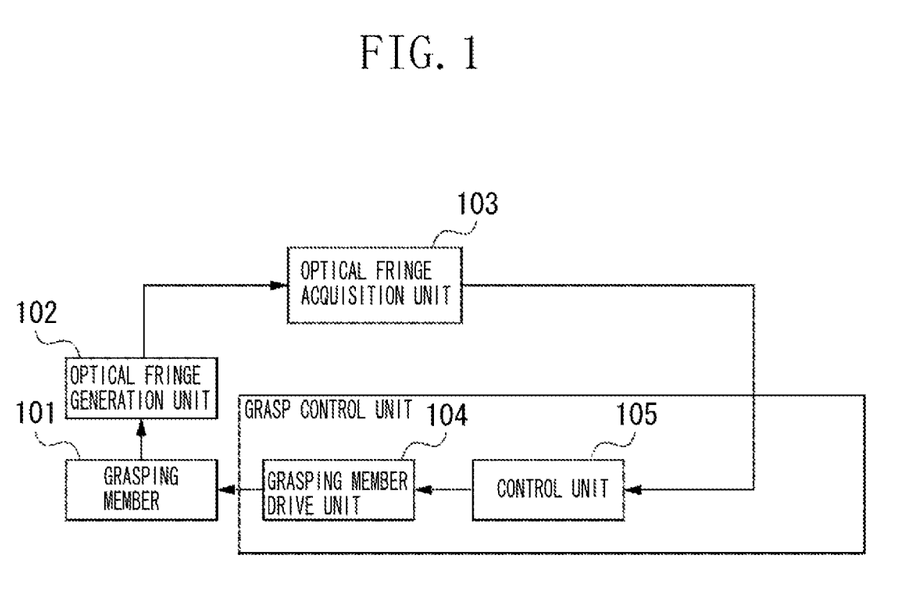
FIG. 1 is a view illustrating a structure of a grasping apparatus that performs grasping control of an operation target body according to a first exemplary embodiment of the present invention.

FIG. 1 is a view illustrating a structure of a grasping apparatus that controls grasping of an operation target body according to a first exemplary embodiment of the present invention. The operation target body is, for example, a part of a product that is grasped in an assembling operation by a robotic arm or the like. In the first exemplary embodiment, the operation performed by the robotic arm is a grasping operation, that is, a pressing operation. Accordingly, the operation target body is a member to be pressed. However, the present invention can be applied to other operations than the pressing operation, and it is not limited to the control of the pressing operation.

A grasping member 101 grasps an operation target body. Hereinafter, a specific structure of the grasping member 101 is described with reference to FIGS. 2A to 2E. FIGS. 2A to 2E are views illustrating grasping mechanisms and parts of the grasping mechanisms that use the grasping member 101 according to the first exemplary embodiment.

Figure 2A:
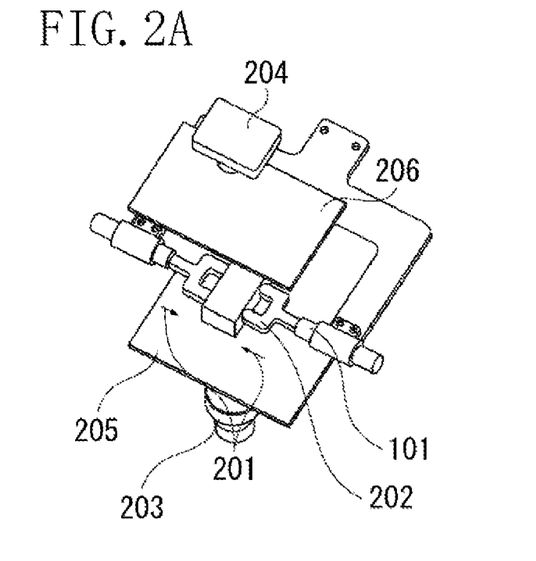
FIGS. 2A to 2E are views illustrating grasping mechanisms according to the first exemplary embodiment of the present invention.
Figure 2B:
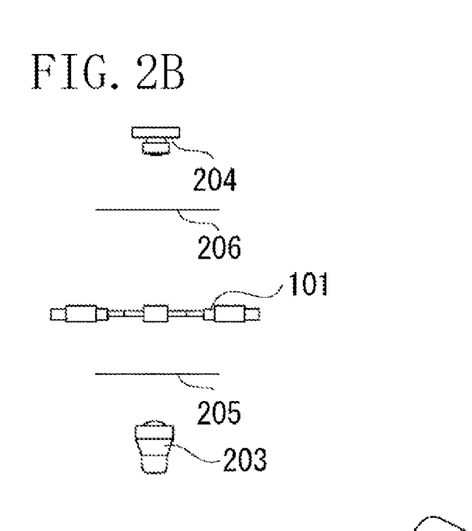

FIG. 2A is a view illustrating a grasping mechanism according to the first exemplary embodiment. FIG. 2B is a view illustrating a side of the grasping mechanism according to the first exemplary embodiment. As illustrated in FIGS. 2A and 2B, a contactor 202 is used to contact an operation target body and grasp the body in a grasping operation of the operation target body.

Figure 2C:
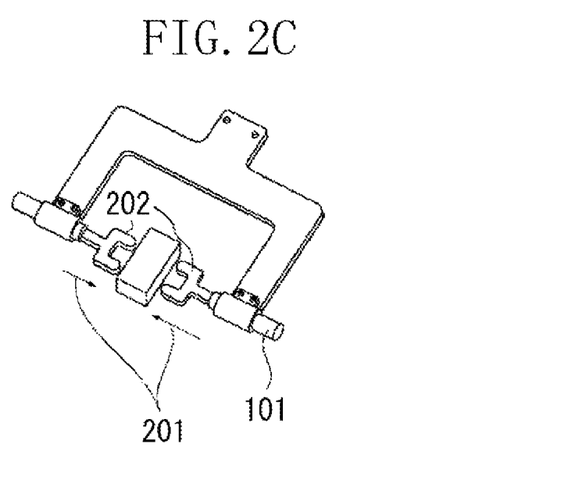
Figure 2D:
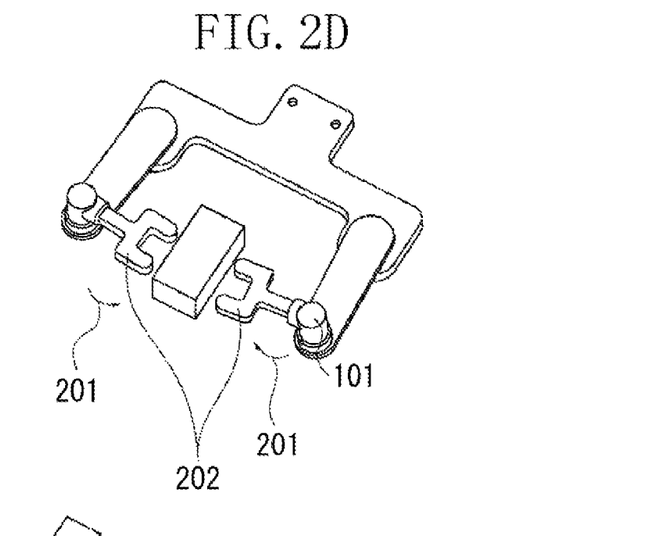

FIG. 2C is a view illustrating the grasping mechanism in operation according to the first exemplary embodiment. FIG. 2D illustrates another view of the grasping mechanism in operation according to the first exemplary embodiment. As illustrated in FIGS. 2C and 2D, it is possible to grasp the operation target body by moving the grasping member 101 in a direction 201. As illustrated in FIG. 2C, the grasping member 101 performs the grasping operation in a translational direction. In FIG. 2D, the grasping member 101 performs the grasping operation in a rotational direction. The grasping member 101 can perform the grasping operation in either direction. The grasping member 101 is connected to a drive motor such as an actuator, and can move in the direction 201 driven by the drive motor.

An optical fringe generation unit 102 generates an optical fringe according to stress strain generated by reaction force when the grasping member 101 grasps an operation target body. The optical fringe generation unit 102 includes, for example, an optical elastic member to generate the optical fringe. The optical elastic member can be formed by placing a member formed of transparent glass or acrylic between two polarizing plates. Further, the optical elastic member can also be formed by applying an optical elastic film to a general grasping member. If the optical elastic film is used, it is not necessary to use the glass or acrylic plates, and a scope of material choices for the grasping member can be broadened. When an external force is applied to the optical elastic member, in a part of the member where stress is generated by the reaction force, strain corresponding to the stress is generated and a molecular structure is changed. Since the molecular structure is changed, if the part of the member where the strain is being generated is irradiated with light, birefringences are generated. The patterns of the birefringences vary depending on the degree of the stress. Since the degrees of the stress vary depending on a part of the member, when a load is applied to the optical elastic member, the birefringences are generated and fringe patterns of the optical fringes are formed. As to the generated optical fringes, it is considered that the fringes having a same color have substantially the same stress. Accordingly, based on the generated fringe patterns, a stress distribution can be calculated. Further, since the colors of the optical fringes correspond to the degrees of the stress, the stress can be calculated by detecting the colors of the optical fringes.

In an area where the density of the optical fringe is high, the stress varies widely. The optical fringes generated on the optical elastic member are referred to as optical elastic fringes. As illustrated in FIG. 2A, if the optical elastic member is used as the contactor 202 when the operation target body is grasped, due to reaction force in the grasping of the operation target body, optical fringes are generated on the contactor 202.

The optical fringe generation unit 102 may generate an optical interference fringe (Newton fringe) as the optical fringe corresponding to the stress. Further, in the optical fringe generation unit 102, the optical interference fringe may be generated by forming a tiny space using a lens and a glass plate and irradiating with white light. By the stress due to the reaction force, the width of the tiny space changes and the optical interference fringe also changes.

Further, in order to apply the optical fringe generation unit 102 to a material that does not transmit light such as metal, an optical elastic film can be attached to the surface to generate an optical fringe corresponding to the stress. Furthermore, if an optical fringe can be generated corresponding to the stress, any member can be used.

Generally, the member that generates an optical fringe is used for the contactor 202 that contacts an operation target body. However, the member may be used at any part in the grasping apparatus where a stress load is applied.

An optical fringe acquisition unit 103 functions as a detection unit that detects an optical fringe. The optical fringe acquisition unit 103 detects an optical fringe generated by the optical fringe generation unit 102 and acquires data of the optical fringe. The optical fringe acquisition unit 103 uses a photodetection sensor for visible light. As illustrated in FIG. 2A, the photodetection sensor includes a light generation device 203 and a CCD sensor 204 that can detect visible light using a CCD element. The light generated by the light generation unit 203 is transmitted through the contactor 202 and detected by the CCD sensor 204. To detect an optical fringe, it is necessary to align wavelengths and directions of light entering an operation target body and light transmitted through the target body. Accordingly, polarization plates are provided in the optical fringe acquisition unit 103. In the first exemplary embodiment, a polarizer 205 and an analyzer 206 function as the polarization plates.

Figure 2E:
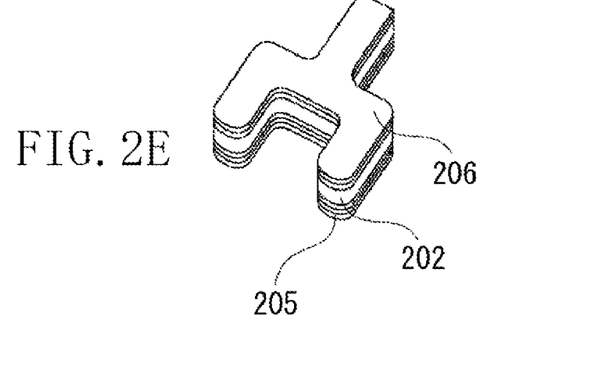

FIG. 2E illustrates the contactor 202 that is integrated with the polarization plates. In the first exemplary embodiment, the grasping mechanism illustrated in FIG. 2A is described. In FIG. 2A, as the polarization plates, the polarizer 205 and the analyzer 206 are used. However, for example, as illustrated in FIG. 2E, a grasping mechanism that uses the contactor 202 sandwiched between the polarizer 205 and the analyzer 206 may be used. When the contactor 202 and the polarization plates are integrated as illustrated in FIG. 2E, it is no longer necessary to provide the polarizer 205 and the analyzer 206 illustrated in FIG. 2A. Accordingly, the grasping apparatus can be downsized in this case.

Further, although the light detection accuracy is decreased, a common video camera may be used as the optical fringe acquisition unit 103. Further, if a device having a certain polarizing property is used as the optical fringe acquisition unit 103, the optical fringe detection accuracy can be improved.

A grasping member drive unit 104 drives the grasping member 101. The grasping member drive unit 104 includes a drive motor and a drive gear. In response to an instruction from outside, the grasping member drive unit 104 drives the drive motor and drives the grasping member 101.

A control unit 105 controls the grasping member drive unit 104 based on the data of the optical fringe acquired by the optical fringe acquisition unit 103. The control unit 105 includes a central processing unit (CPU), and a random access memory (RAM) that stores a drive control program and a data analysis program.

When the grasping member drive unit 104 is controlled, first, the CPU reads the drive control program from the RAM. Then, according to the drive control program, in order to perform a predetermined operation (e.g., grasping an operation target body), the CPU sends a drive signal to the grasping member drive unit 104.

Meanwhile, the CPU reads the data analysis program from the RAM. Then, the CPU analyzes the data of the optical fringe using the data analysis program. As a result of the analysis, for example, if stress being generated at the grasping member 101 is greater than a tolerance that is set in advance, the CPU stops the drive signal that is to be sent to the grasping member drive unit 104. To control the grasping member drive unit 104, methods other than the above-described method may be used. The other control methods are described below.

Figure 3:
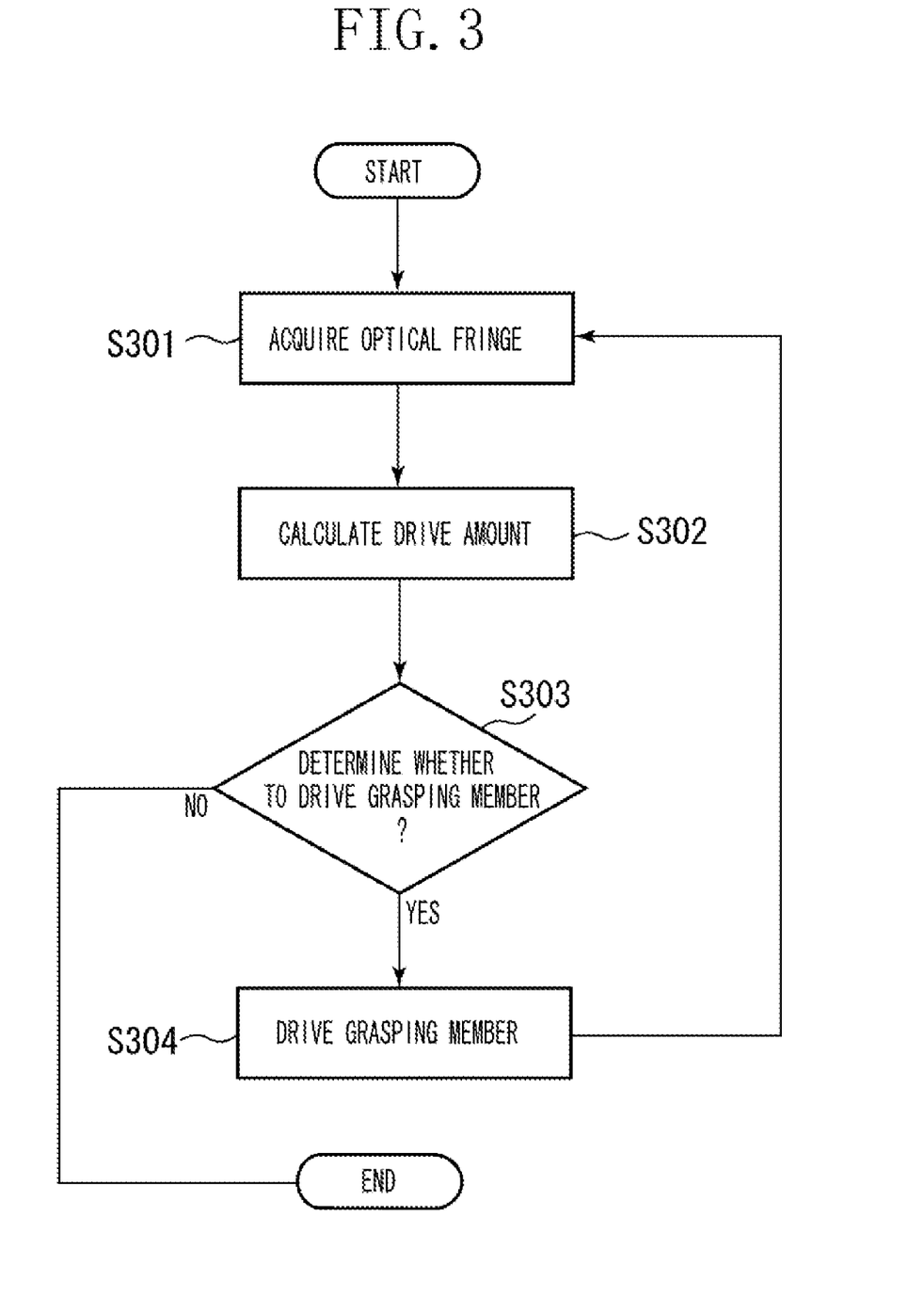
FIG. 3 is a view illustrating a flow of a control process of a grasping operation according to the first exemplary embodiment of the present invention.

FIG. 3 is a flowchart illustrating the control process of the grasping operation according to the first exemplary embodiment. With reference to FIG. 3, the control process of the grasping operation according to the first exemplary embodiment is described. Each process in FIG. 3 is performed by operation of each element in the grasping apparatus in FIG. 1.

In step S301, the optical fringe acquisition unit 103 acquires data of an optical fringe generated on the optical fringe generation unit 102.

In step S302, the control unit 105 calculates a drive amount for driving the grasping member. In the first exemplary embodiment, the control unit 105 calculates a drive amount of the grasping member 101 for the grasping operation based on an optical fringe. The method for calculating the drive amount of the grasping member 101 based on the optical fringe generated by the optical fringe generation unit 102 is described below.

FIGS. 4A to 4D illustrate optical fringes generated on the contactor 202 respectively according to the first exemplary embodiment. The control unit 105 determines a state of the contactor 202 from among the states illustrated in FIGS. 4A to 4D, and calculates the drive amount.

Figure 4A:
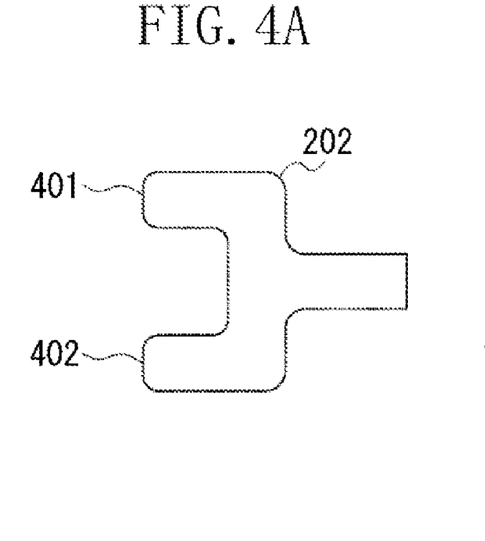
FIGS. 4A to 4D are views illustrating optical fringes generated on a contactor according to the first exemplary embodiment of the present invention in detail.

FIG. 4A illustrates a state where no optical fringe is generated on the contactor 202. When no optical fringe is generated, the contactor 202 is not in contact with the operation target body, and stress is not generated on the contactor 202. In this state, the control unit 105 calculates a drive amount so that the grasping member 101 is driven in a grasping direction.

Figures 4B, 4D:
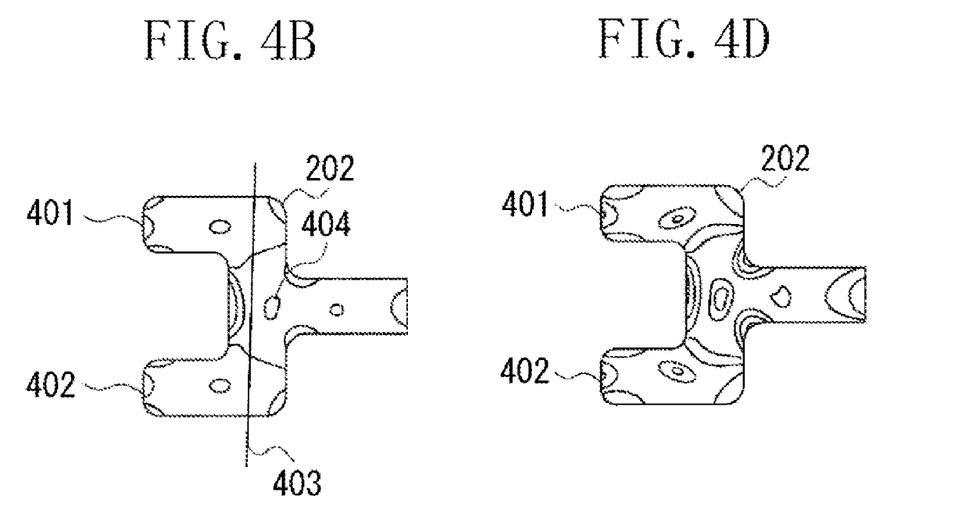

FIG. 4B illustrates optical fringes generated on the contactor 202. When the optical fringes are generated, the contactor 202 is in contact with the operation target body and the grasping member 101 is grasping the operation target body. In this state, the grasping operation is completed. Therefore, it is not necessary to drive the grasping member 101, and the control unit 105 sets the drive amount to zero.

Figure 4C:
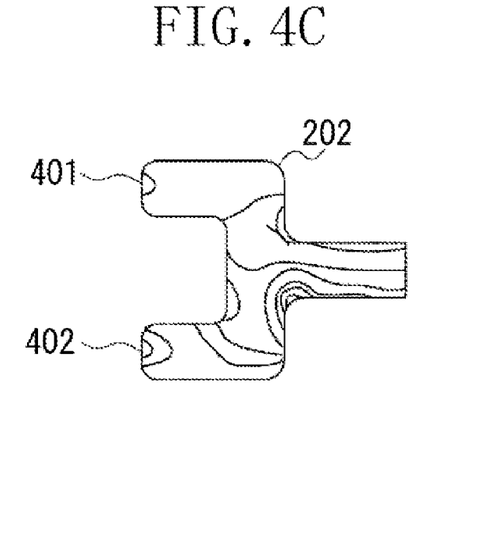

FIG. 4C illustrates a state where more optical fringes are generated around an end portion 402 of the contactor 202 than around an end portion 401. When the optical fringes are generated around the end portion 402, stress is generated intensively around the end portion 402. This implies an unbalanced state. For example, the operation target body is being grasped only by the end portion 402, and not appropriately grasped. In this case, it is necessary to start the grasping operation from the beginning again. Accordingly, the control unit 105 calculates the drive amount so that the grasping member 101 is driven in a direction opposite to the grasping direction.

FIG. 4D illustrates a state where many optical fringes are generated on the contactor 202. When many optical fringes are generated, that implies that excessive stress is generated on the contactor 202. Then, it is necessary to loosen the grasping force. Accordingly, the control unit 105 calculates the drive amount so that the grasping member 101 is driven in a direction opposite to the grasping direction.

The control unit 105 determines a state of the contactor 202 from among the states illustrated in FIGS. 4A to 4D by performing an image processing on the image data of the optical fringes acquired by the optical fringe acquisition unit 103. More specifically, the control unit 105 obtains characteristic patterns of the optical fringes in the states of FIGS. 4A to 4D respectively. Then, the control unit 105 extracts a pattern of the optical fringes from the image data, and calculates a degree of similarity between the extracted pattern and the patterns obtained in advance. Finally, the control unit 105 determines a most similar pattern to the extracted pattern from the patterns of FIGS. 4A to 4D, and determines the state of the most similar pattern as the current state.

With respect to the methods of extracting a pattern from the image data, various methods have been proposed. Accordingly, the descriptions of the methods are omitted.

When the pattern is detected, in order to speed up the processing, the status may be determined using only an image of a predetermined area.

In step S303, the control unit 105 determines whether to drive the grasping member 101. If the drive amount calculated in step S302 is zero (NO in step S303), the control unit 105 performs a stop process to finish the grasping operation. If the drive amount is not zero (YES in step S303), the process proceeds to step S304 to drive the grasping member 101.

In step S304, the control unit 105 sends a drive instruction to the grasping member drive unit 104 based on the drive amount calculated in step S302 and instructs the grasping member drive unit 104 to drive the grasping member 101. When the grasping member is driven, the state of the contactor 202 is changed. Accordingly, the process returns to step S301 and the optical fringe is acquired.

Thus, according to the processes from step S301 to step S304, the grasping control based on the optical fringes can be performed. In the first exemplary embodiment, the member that generates optical fringes corresponding to reaction force of grasping force is used. Accordingly, it is not necessary to provide a stress detection sensor or the like in the contactor of the grasping member 101 to determine grasping states. Therefore, in the grasping apparatus of the first exemplary embodiment, the grasping member 101 can be simplified. Further, since the apparatus can be configured using the member that generates optical fringes, and a common video camera, the production cost can be reduced as compared with that of apparatuses that use a stress detection sensor or the like.

Further, in the process of step S302, the image data of the optical fringes generated on the contactor is acquired as two-dimensional data to perform the image processing. However, this process can be simplified. For example, a predetermined line area 403 illustrated in FIG. 4B can be set. Then, the optical fringe acquisition unit 103 acquires visible light data only from the line area 403, using a visible light line sensor that captures visible light of the two-dimensional line area. Then, the visible light data of the line area 403 is processed, and a state of the data is determined from among the states of FIGS. 4A to 4D. The target of the data processing is not two-dimensional image data but one-dimensional line data so that the processing can be speeded up. To further speed up the processing, a predetermined point 404 may be set and the processing can be similarly performed using a visible light point sensor that captures visible light of the predetermined point 404. Further, similar processing can also be performed using an area other than the line area, or the point.

In the process of step S302, the image processing is performed on the image data of the optical fringes and a state of the contactor 202 is determined from among states of FIGS. 4A to 4D. However, it may be possible that the state is not determined. Instead of making the determination from image data of optical fringes, a stress distribution of stress generated on the contactor can be calculated, and based on the calculated stress distribution, a drive amount may be calculated.

When the stress is calculated from the image data of the optical fringes, information about correspondence between stress and patterns or colors of the optical fringes is required. For example, a stress test using the grasping member 101 can be performed, and based on experiment data of the test, information about the correspondence between the stress and the patterns or the colors of the optical fringes may be obtained. Further, the correspondence between the stress and the patterns or the colors of the optical fringes may be obtained by numeric calculation using a finite element method. As described above, based on optical fringes having a same color, it can be considered that substantially the same stress is generated at the optical fringes. Accordingly, by drawing lines along the areas of the same colors, stress lines based on the optical fringes can be drawn so that a stress distribution is obtained. Using the stress distribution, stress generated in the predetermined area on the contactor 202 can be calculated in detail. Accordingly, more accurate grasping control can be performed based on the stress.

As described above, according to the pressing apparatus of the first exemplary embodiment, when optical fringes generated by reaction force of pressure are used, the structure of the apparatus can be simplified as compared with grasping apparatuses that use contact type pressure sensors.

Further, in the first exemplary embodiment, the grasping control is performed using only optical fringes. However, for example, in addition to the optical fringe detection, a marker that detects a positional attitude may be provided in the grasping member 101. A positional attitude of the grasping member 101 may be detected by the marker so that more accurate grasping control can be performed. Further, by forming the grasping member 101 in a unique shape, the positional attitude of the grasping member 101 can also be detected without providing the marker.

Second Exemplary Embodiment

In a second exemplary embodiment of the present invention, a control of a grasping apparatus is performed by capturing an image of an operation target body and the grasping member 101 using a video camera or the like, and based on the captured image.

Figure 5:
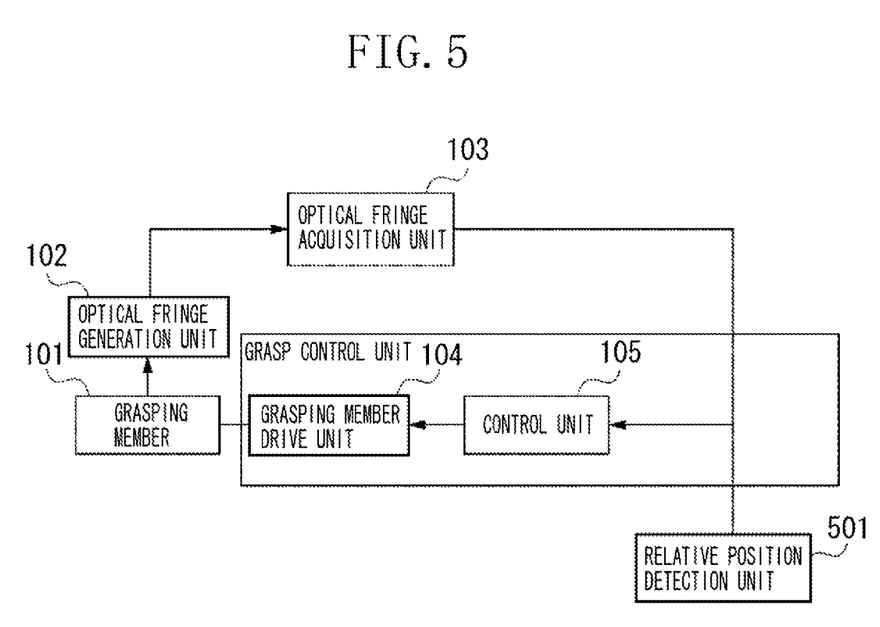
FIG. 5 is a view illustrating a structure of a grasping apparatus according to a second exemplary embodiment of the present invention.

FIG. 5 illustrates a structure of a grasping apparatus according to the second exemplary embodiment. The structure of the apparatus is similar to that of the apparatus illustrated in FIG. 1 according to the first exemplary embodiment. The apparatus according to the second exemplary embodiment differs from the apparatus illustrated in FIG. 1 in that the apparatus includes a relative position detection unit 501.

The relative position detection unit 501 is an imaging device that captures a visible image of the grasping member 101 and an operation target body. The relative position detection unit 501 includes a video camera that can capture a visible image, and captures images of the grasping member 101 and the operation target body. The captured visible images are sent to the control unit 105.

The control unit 105 has substantially the same functions as the control unit 105 according to the first exemplary embodiment. The control unit 105 includes a CPU and a RAM that stores a drive control program and a data analysis program.

The second exemplary embodiment is different from the first exemplary embodiment in that the grasping member drive unit 104 is controlled based on data of optical fringes acquired by the optical fringe acquisition unit 103, and the visible image captured by the relative position detection unit.

Figure 6:
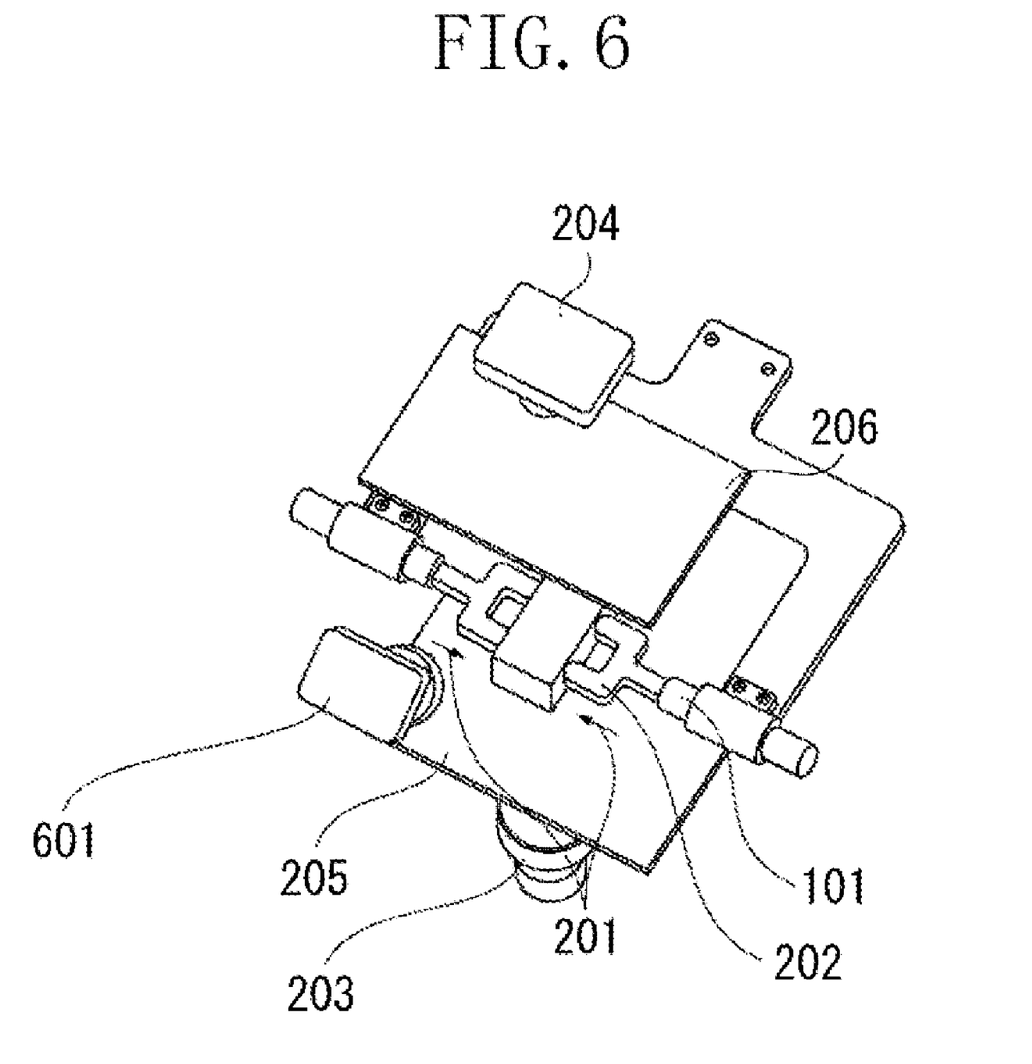
FIG. 6 is a view illustrating a structure of a grasping mechanism according to the second exemplary embodiment of the present invention.

FIG. 6 illustrates a structure of the grasping apparatus according to the second exemplary embodiment. Similar to the structure of the apparatus illustrated in FIG. 5, the structure illustrated in FIG. 6 has substantially the same structure to FIG. 2A. A different point is that the apparatus includes a video camera 601 serving as the relative position detection unit 501.

Figure 7:
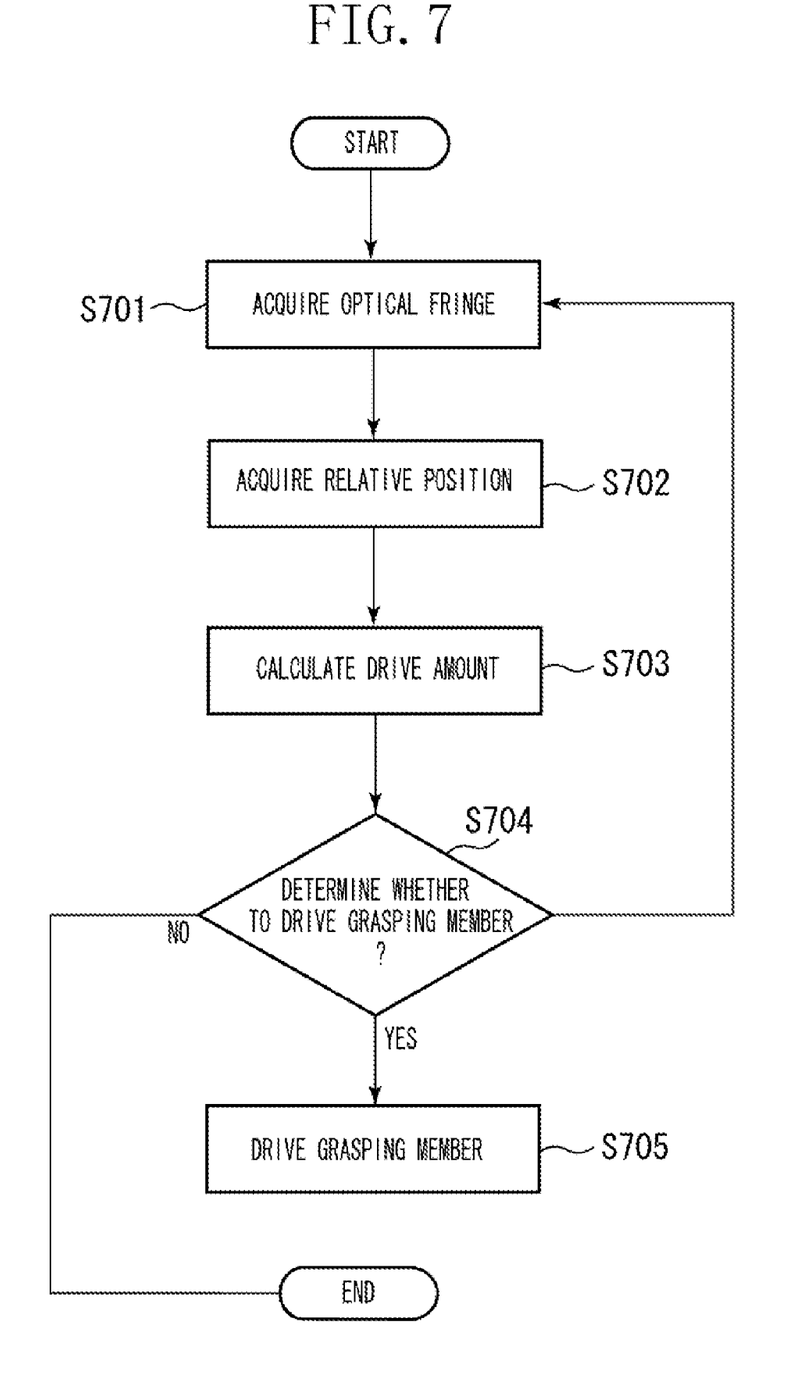
FIG. 7 is a view illustrating a flow of a control process of a grasping operation according to the second exemplary embodiment of the present invention.

FIG. 7 is a flowchart illustrating a flow of a grasping control according to the second exemplary embodiment. The process illustrated in FIG. 7 is similar to FIG. 3. The process is performed by operation of each element in the grasping apparatus of FIG. 5.

In step S701, similar to step S301 of FIG. 3, the optical fringe acquisition unit 103 acquires data of optical fringes generated on the optical fringe generation unit 102.

In step S702, the relative position detection unit 501 captures an image of the grasping member 101 and the operation target body to acquire a visible image.

In step S703, the control unit 105 calculates a drive amount for driving the grasping member. In the second exemplary embodiment, the control unit 105 calculates a drive amount of the grasping member 101 for the grasping operation based on the optical fringes and the visible image acquired by the relative position detection unit 501. Hereinafter, a method for calculating the drive amount of the grasping member 101 based on the optical fringes generated on the optical fringe generation unit 102, and the visible image acquired by the relative position detection unit 501, is described.

The control unit 105 calculates a distance between the contactor 202 and the operation target body by analyzing the data of the visible image captured by the relative position detection unit 501. If the calculated distance is longer than a value set in advance, it is possible to determine that the contactor 202 is fully separated from the operation target body. Accordingly, the control unit 105 calculates a drive amount for driving the grasping member 101 in a grasping direction without analyzing the optical fringe.

If the distance between the contactor 202 and the operation target body is short, the control unit 105 calculates the drive amount of the grasping member 101 in a similar method to the first exemplary embodiment using the optical fringe data of the contactor 202.

As described above, by using the visible image detected by the relative position detection unit 501, more appropriate drive amount can be calculated. Further, other control methods using the visible image acquired by the relative position detection unit 501 may be used.

In steps S704 and S705, processes similar to steps S303 and S304 in FIG. 3 are performed.

In the second exemplary embodiment, as the relative position detection unit 501, the video camera 601 is used and the visible image of the grasping member 101 and the operation target body is acquired. However, the visible image of the grasping member 101 and the operation target body may also be acquired using the CCD sensor 204 that functions as the optical fringe acquisition unit 103. When the CCD sensor 204 is used, the video camera 601 does not need to be provided, and therefore, the grasping apparatus can be simplified.

Further, to calculate the drive amount with a high degree of accuracy, a plurality of CCD sensors 204 and the light generation devices 203 may be used.

Figure 8:
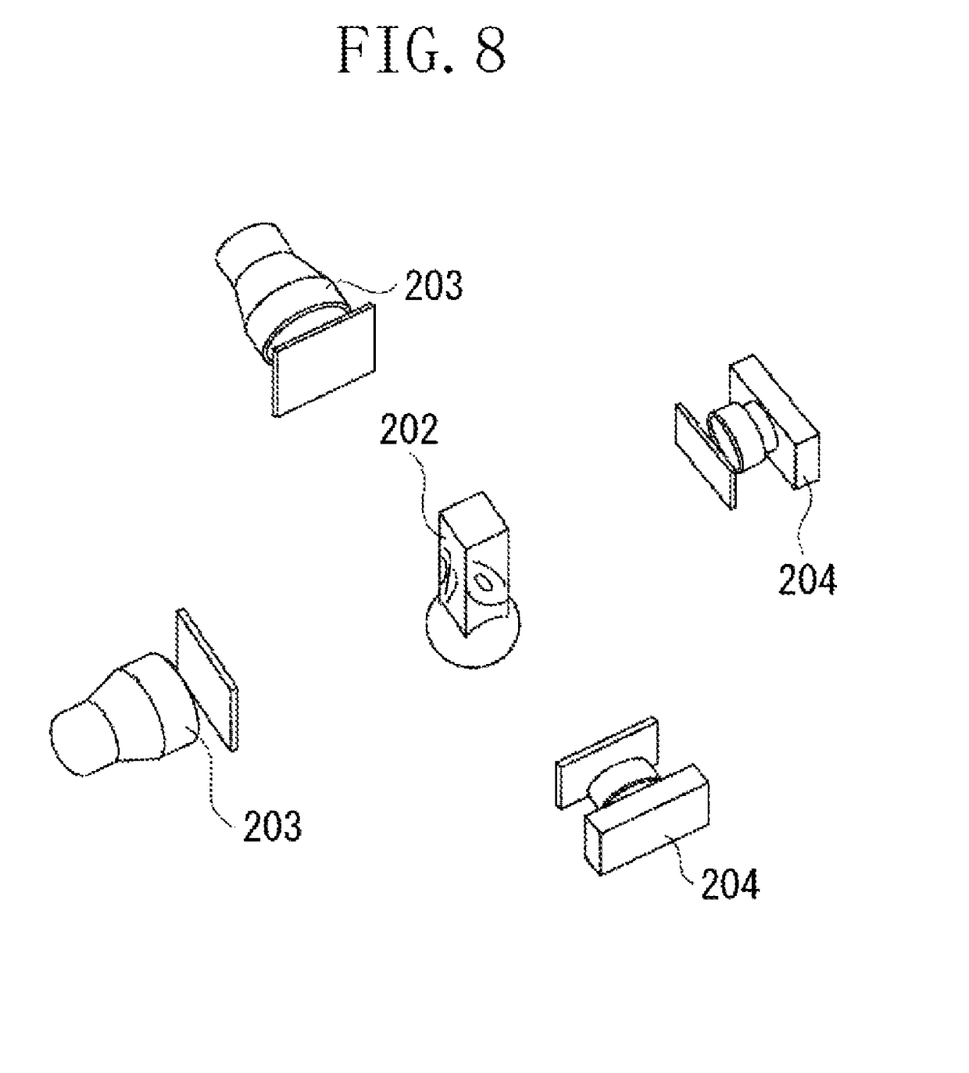
FIG. 8 is a view illustrating an apparatus that has two pairs of charge coupled device (CCD) sensors and light generation devices according to the second exemplary embodiment of the present invention.

FIG. 8 is a view illustrating an apparatus that has two pairs of the CCD sensors 204 that function as the optical fringe acquisition units 103 and the light generation devices 203. As illustrated in FIG. 8, if the plurality of CCD sensors 204 and the light generation devices 203 are provided, it is possible to detect optical fringes from at least two directions and acquire a plurality of pieces of optical fringe data. By using the plurality of pieces of optical fringe data, a three-dimensional stress distribution can be calculated, and it is possible to calculate the drive amount of the grasping member 101 with a higher degree of accuracy. Further, even if the image captured from one direction is interrupted by an obstacle, if the image can be captured from the other direction, it is possible to detect the optical fringes and perform the grasping control.

As described above, according to the second exemplary embodiment, by using the visible data other than the optical fringe data or the plurality of pieces of optical fringe data to control the grasping member 101, the control can be performed with a higher degree of accuracy.

Third Exemplary Embodiment

A structure of an apparatus and a control method according to a third exemplary embodiment are similar to the first and second exemplary embodiments. The apparatus according to the third exemplary embodiment differs from the apparatuses according to the first and second exemplary embodiments in a structure of the contactor 202 that contacts an operation target body.

Figure 9:
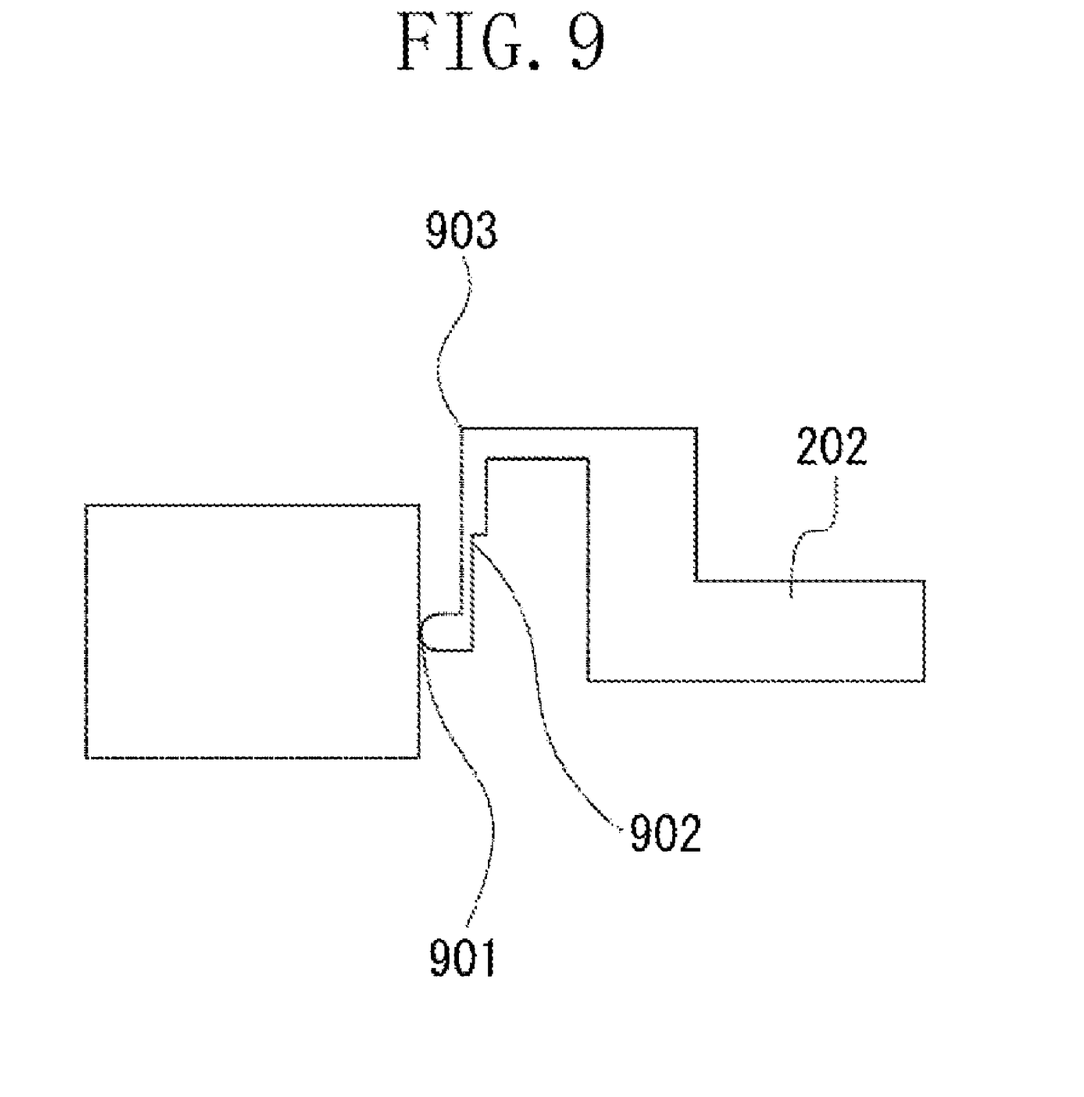
FIG. 9 is a view illustrating a contactor that has a notched part according to a third exemplary embodiment of the present invention.

FIG. 9 is a view illustrating a shape of the contactor 202 according to the third exemplary embodiment.

At a contact point 901, the contactor 202 makes contact with an operation target body in a pressing operation such as grasping. A first notched part 902 and a second notched part 903 are provided in the contactor 202.

The contactor 202 has the first notched part 902 above the contact point 901 where the contactor 202 makes contact with the operation target body. As understood from the drawing, the width of the contactor 202 becomes broader from the first notched part 902. The width of the contactor 202 further becomes broader from the second notched part 903. When the contactor 202 having such a structure is used, for example, if a load of a predetermined value or less is applied to the contactor 202 from the contact point 901, a part around the first notched part 902 is bent under the load and an optical fringe is generated around the first notched part 902. If a load of the predetermined value or more is applied to the contactor 202, a part around the second notched part 903 is bent under the load and an optical fringe is generated around the second notched part 903. Accordingly, the optical fringe acquisition unit 103 can stepwise evaluate the load generated on the contactor 202 by detecting the optical fringes from the first notched part 902 and the second notched part 903.

FIGS. 10A to 10D are views illustrating the contactor 202 that has beam parts.

Figure 10A:
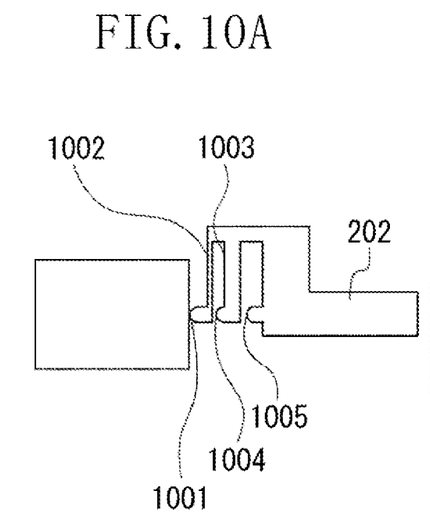
FIGS. 10A to 10D are views illustrating a contactor that has beam parts according to the third exemplary embodiment of the present invention.

FIG. 10A illustrates a state where the contactor 202 having the beam parts is in contact with an operation target body.

At a first contact point 1001, the contactor 202 is in contact with the operation target body. The contactor 202 includes a first beam part 1002 that is bent under a load. Similarly, the contactor 202 includes a second beam part 1003 that is bent under a load. At a second contact point 1004, when the first beam part 1002 is bent, the first beam part 1002 contacts the second beam part 1003. A third contact point 1005 contacts the second beam part 1003 when the second beam part 1003 is bent.

Figure 10B:
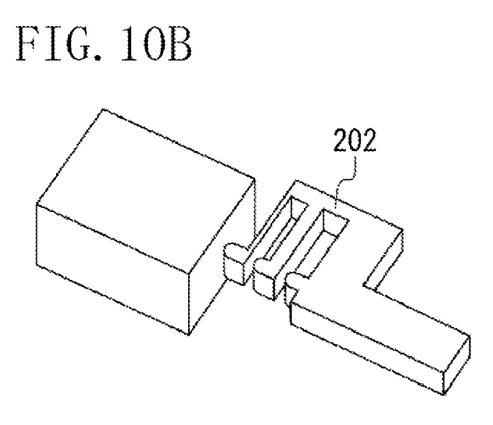

FIG. 10B is a perspective view illustrating an obliquely viewed contactor 202 of FIG. 10A. The beam parts are easily damaged. Accordingly, as illustrated in FIG. 10B, if the beam parts are formed to have some thickness, a degree of safety of the apparatus can be improved.

Figure 10C:
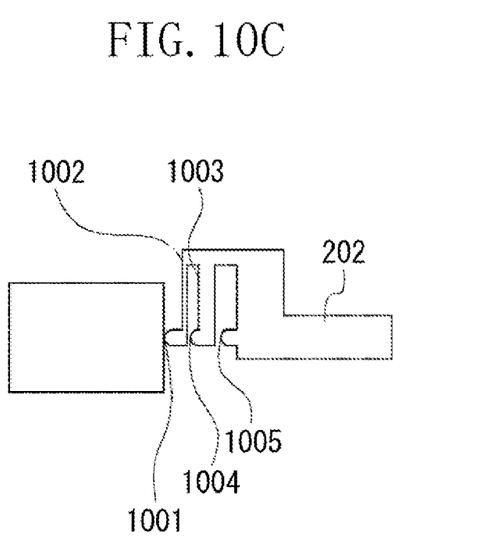

FIG. 10C illustrates a state where the contactor 202 presses the operation target body and the first beam part 1002 is bent.

Figure 10D:
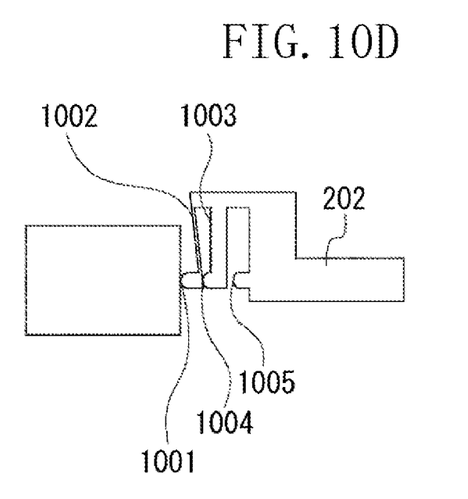

In FIG. 10D, the first beam part 1002 is bent, and the first beam part 1002 contacts the second beam part 1003 at the second contact point 1004. The first beam part 1002 is bent as illustrated in FIG. 10C. If a load exceeding a predetermined value is applied, the first beam part 1002 contacts the second contact point 1004. When the first beam part 1002 contacts the second contact point 1004, an optical fringe owing to the load is generated at the second contact point 1004. If more load is added, the second beam part 1003 is similarly bent, and the second beam part 1003 contacts the third contact point 1005. When the second beam part 1003 contacts the third contact point 1005, an optical fringe is generated at the third contact point 1005.

As described above, by pressing with the contactor 202 illustrated in FIG. 10A, and detecting the contact points of the beam parts with the optical fringe acquisition unit 103, the load applied to the contactor 202 can be stepwise calculated.

FIGS. 11A to 11D illustrate states where the contactor 202 having an L shape is in contact with an operation target body. At a contact point 1101, the contactor 202 makes contact with the operation target body.

Figure 11A:
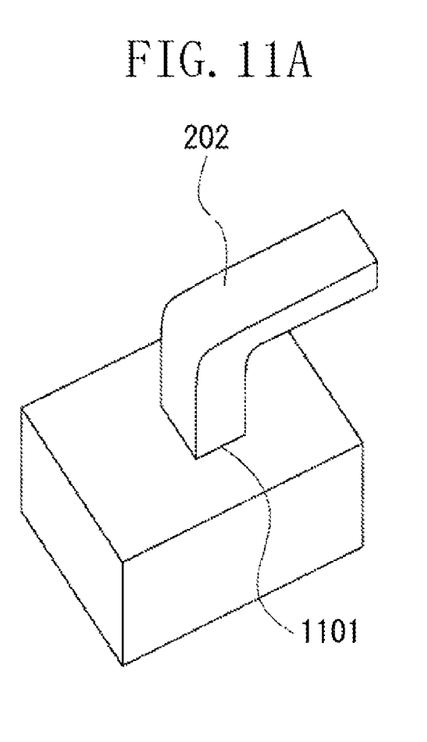
FIGS. 11A to 11D are views illustrating an L-shaped contactor that is in contact with an operation target body according to the third exemplary embodiment of the present invention.
Figure 11B:
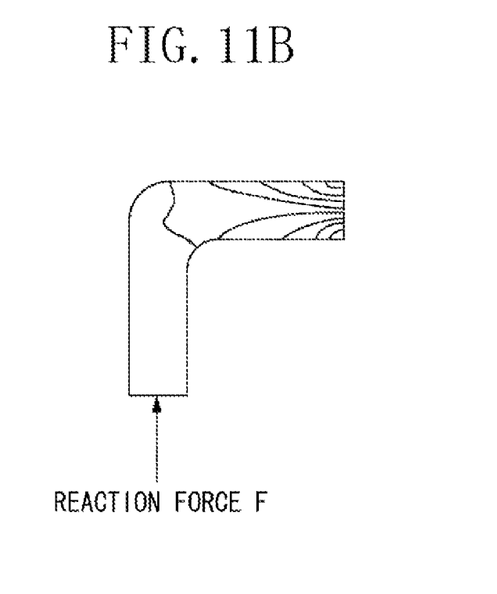

FIG. 11B illustrates a state where a load is applied to the contact point 1101 in a vertical direction and reaction force is generated in the vertical direction.

Figure 11C:
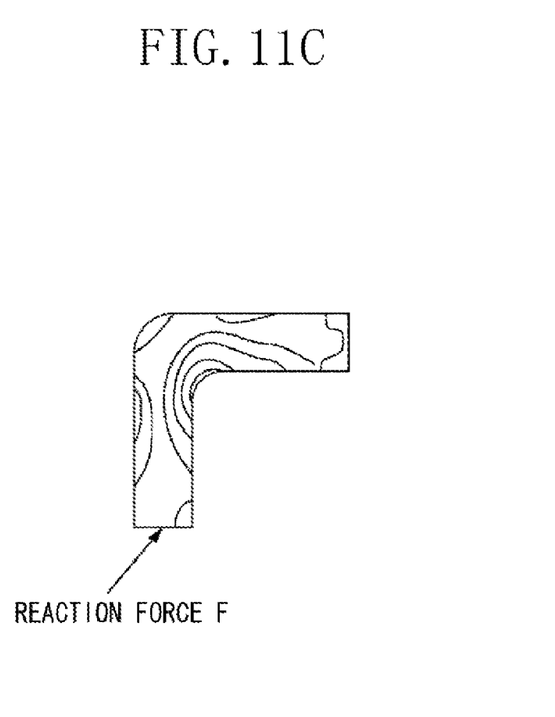

FIG. 11C illustrates a state where a load is applied to the contact point 1101 in a left oblique direction and reaction force is generated in the oblique direction.

Figure 11D:
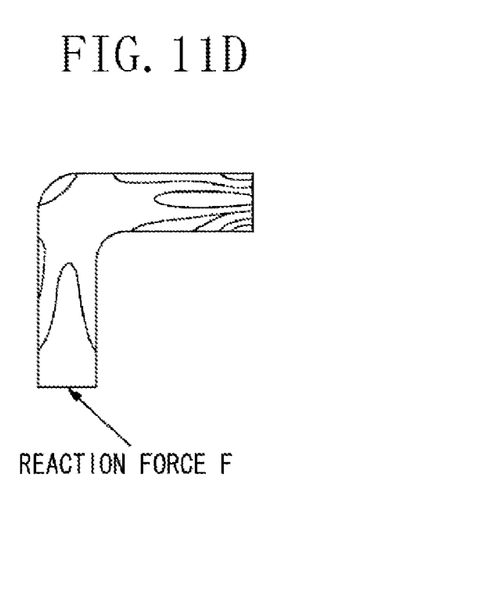

FIG. 11D illustrates a state where a load is applied to the contact point 1101 in a right oblique direction and reaction force is generated in the oblique direction.

In FIGS. 11A to 11D, the contactor 202 has the L shape. The optical fringes generated on the L-shaped contactor 202 characteristically vary according to the directions of the reaction force.

Accordingly, by detecting the characteristic patterns of the optical fringes using the method described in the first exemplary embodiment, it is possible to calculate a loading direction applied to the contact point.

When a pressure is applied to an operation target body, it is important to detect whether the contactor slides over the operation target body. Here, an angle (hereinafter, referred to as a force angle) formed by a reaction force F and the contact point 1101 is $\alpha$ (in FIG. 11B, $\alpha=90°$), and a coefficient of friction of the contactor 202 and the operation target body is $\mu$. Then, a condition that the contactor 202 starts to slide is, $$F \times \cos(\alpha) < F \times \sin(\alpha) \times \mu.$$

The expression can be further simplified as follows:

$$1 < \mu \tan(\alpha).$$

Accordingly, if a coefficient of friction and a contact force angle are obtained, it is possible to determine whether the contactor 202 starts to slide. Thus, a condition that the contactor starts to slide can be calculated by detecting an optical fringe using the optical fringe acquisition unit 103 and based on the detected data of the optical fringe, and by calculating a reaction force using the control unit 105. As described above, according to the third exemplary embodiment, the grasping member 101 can be controlled to slide the contactor 202 or to prevent the contactor 202 from starting to slide.

Figure 12A:
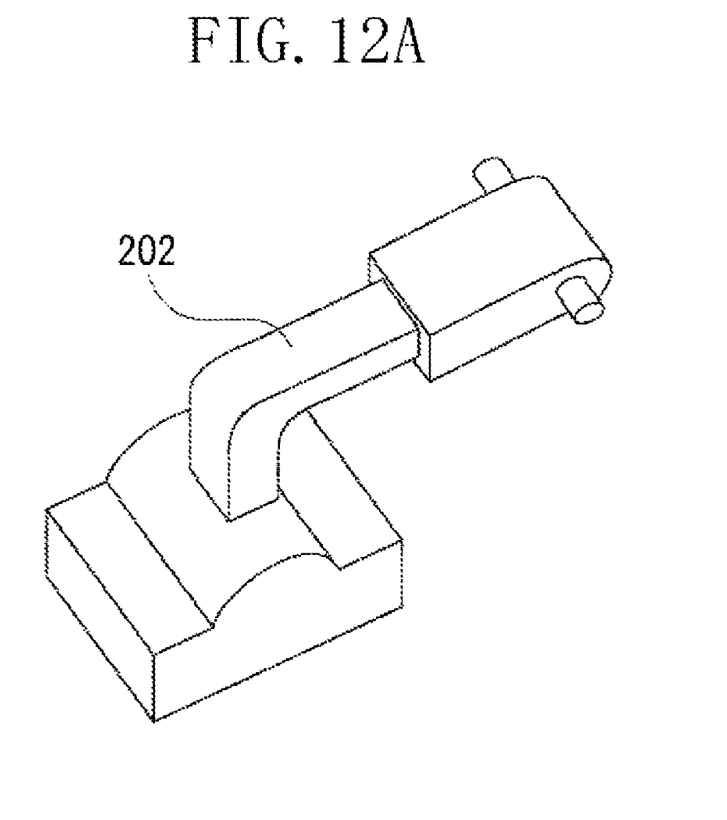
FIGS. 12A and 12B are views illustrating an L-shaped contactor that is in contact with an operation target body according to the third exemplary embodiment of the present invention.

FIG. 12A illustrates a state that the L-shaped contactor 202 is in contact with an operation target body.

Figure 12B:
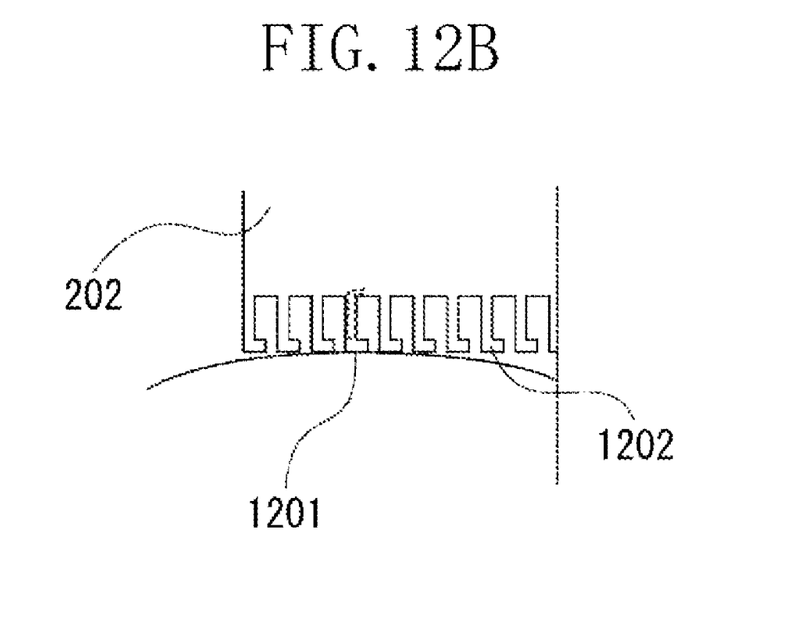

FIG. 12B illustrates the contact state of the L-shaped contactor 202 and the operation target body. At a contact point 1201, the contactor 202 contacts an operation target body. A beam part 1202 is a beam-shaped member provided at the contact part of the contactor 202. Similar to the contactor 202, the beam part 1202 is formed of a member that generates an optical fringe according to stress. The contactor 202 includes a plurality of the beam members 1202 on a contact surface where the contactor 202 makes contact with the operation target body. Accordingly, an optical fringe is generated only on the beam member 1202 that contacts the operation target body. If the beam members 1202 are not provided as in the case of FIG. 12A, a position of the contact point can be calculated based on an optical fringe generated on the contactor 202. However, as illustrated in FIG. 12B, by disposing the plurality of beam members 1202 on the contact surface of the contactor 202, it is possible to calculate the position of the contact point with a higher degree of accuracy.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed:

1. An optical fringe generation member control apparatus comprising:
    a member, on which an optical fringe is generated by stress in the member, includes a pressure unit configured to press a member to be pressed;
    a detection unit configured to detect optical fringe; and
    a control unit configured to control operation of the member on which the optical fringe is generated, based on a detection result by the detection unit,
    wherein the pressure unit includes a first optical fringe member and a second optical fringe member that is bent by a reaction force generated when the pressure unit presses the member to be pressed and that contacts the first optical fringe member, and
    wherein the detection unit detects an optical fringe generated by the contact of the first optical fringe member and the second optical fringe member.

2. The optical fringe generation member control apparatus according to claim 1, further comprising:
    an acquisition unit configured to acquire information about correspondence between the detected optical fringe and stress; and
    a calculation unit configured to calculate a stress distribution of the stress generated on the member on which the optical fringe is generated, based on the detected optical fringe and the acquired correspondence information between the detected optical fringe and the stress,
    wherein the control unit is configured to control the operation of the member on which the optical fringe is generated, based on the calculated stress distribution.

3. The optical fringe generation member control apparatus according to claim 2, wherein the control unit is configured to reduce a pressure of the pressure unit if a stress greater than a tolerance set in advance is generated in the calculated stress distribution.

4. The optical fringe generation member control apparatus according to claim 2,
    wherein the detection unit includes a line sensor, and detects an optical fringe in a line area detectable by the line sensor, and
    wherein the calculation unit is configured to calculate the stress of the member on which the optical fringe is generated, based on the detected optical fringe in the line area.

5. The optical fringe generation member control apparatus according to claim 1, further comprising a second detection unit configured to detect a relative position between the member to be pressed and the pressure unit,
    wherein the control unit is configured to control the pressure of the pressure unit based on a detection result by the detection unit and a detection result by the second detection unit.

6. The optical fringe generation member control apparatus according to claim 1,
    wherein the detection unit is configured to acquire an image of the optical fringe, and
    the optical fringe generation member control apparatus further comprising:
    an area extraction unit configured to extract a predetermined area from the image acquired by the detection unit, and
    a calculation unit configured to calculate a stress distribution of the pressure unit from an optical fringe in the extracted area.

7. The optical fringe generation member control apparatus according to claim 1, further comprising a slide condition calculation unit configured to estimate a condition that the pressure unit starts to slide over the member to be pressed based on a coefficient of friction of the member to be pressed and the pressure unit,
    wherein the control unit is configured to control the slide of the member to be pressed and the pressure unit based on a calculated condition and a detection result by the detection unit.

8. The optical fringe generation member control apparatus according to claim 1, wherein the detection unit is configured to detect an optical fringe from at least two directions of the pressure unit, the optical fringe generation member control apparatus further comprising a calculation unit configured to calculate a stress distribution of stress generated on the pressure unit based on the optical fringe detected from at least two directions and the acquired correspondence information.

9. A method of controlling an optical fringe generation member, the method comprising:
    pressing a member to be pressed;
    detecting an optical fringe;
    controlling operation of a member on which the optical fringe is generated, based on a detection result of the detecting step;
    bending a first optical fringe member and a second optical fringe member by a reaction force generated when the member to be pressed is pressed in the pressing step and that contacts the first optical fringe member; and
    detecting an optical fringe generated by the contact of the first optical fringe member and the second optical fringe member.

10. A computer-readable medium storing a computer program of instructions which cause the computer to perform the method according to claim 9.

* * * * *